United States Patent [19]

Styring, Jr.

[11] 4,311,495

[45] Jan. 19, 1982

[54] SEPARATING CARBON DIOXIDE AND ETHANE BY LIQUID-LIQUID EXTRACTION

[75] Inventor: Ralph E. Styring, Jr., Dallas, Tex.

[73] Assignee: Atlantic Richfield Company, Los Angeles, Calif.

[21] Appl. No.: 108,202

[22] Filed: Dec. 28, 1979

[51] Int. Cl.$^3$ ................................................. F25J 3/02
[52] U.S. Cl. ............................................. 62/17; 62/28
[58] Field of Search ......................... 62/17, 20, 23–28

[56] References Cited

U.S. PATENT DOCUMENTS

| | | | |
|---|---|---|---|
| 3,595,782 | 7/1971 | Bucklin et al. | 62/38 |
| 4,012,212 | 3/1977 | Kniel | 62/38 |
| 4,035,167 | 7/1977 | Starks | 55/84 |
| 4,185,978 | 1/1980 | McGalliard | 62/38 |

Primary Examiner—Norman Yudkoff
Attorney, Agent, or Firm—M. David Folzenlogen

[57] ABSTRACT

A method is disclosed for separating a mixture of carbon dioxdie and ethane derived from a prior separation stage. The separation is accomplished by liquid-liquid extraction of a liquefied azeotrope of carbon dioxide and ethane with a liquid hydrocarbon having at least three carbon atoms, that is, propane, or a heavier hydrocarbon, or a mixture of hydrocarbons. The liquid-liquid extraction unit may be preceded by distillation of a carbon dioxide-ethane mixture to form the azeotrope. The ethane and extraction hydrocarbon may be separated in a subsequent distillation stage. The method is useful in carbon dioxide separation facilities where it is desirable to recover ethane that would otherwise be lost.

4 Claims, 1 Drawing Figure

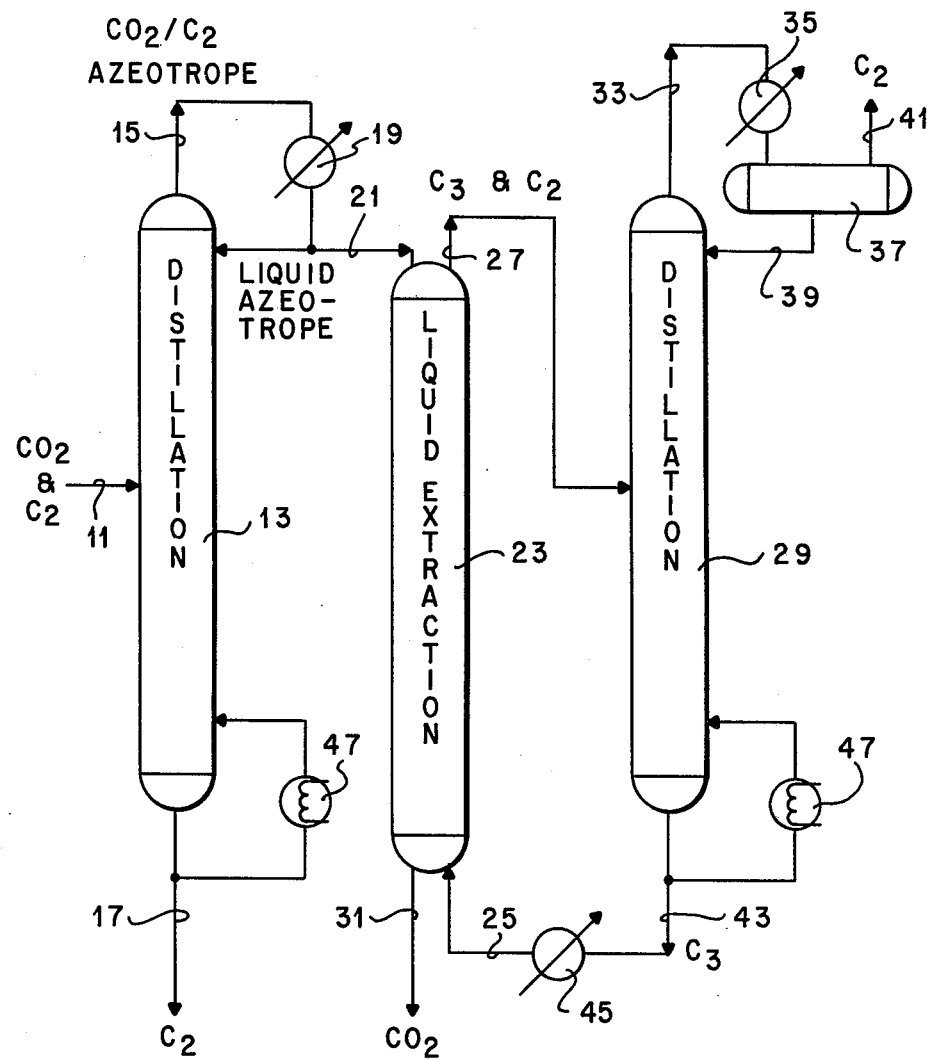

SEPARATING CARBON DIOXIDE AND ETHANE BY LIQUID-LIQUID EXTRACTION

BACKGROUND OF THE INVENTION

This invention is concerned with the separation of a mixture of carbon dioxide and ethane derived from a prior separation or recovery stage or process. More particularly, the invention pertains to separation of a carbon dioxide-ethane azeotrope by liquid-liquid extraction using propane or a heavier hydrocarbon.

It is sometimes desirable to separate carbon dioxide from a gaseous mixture containing ethane, for example, in the treatment of natural gas or a reservoir injection gas, or in the preparation of synthetic natural gas. In one or more stages of these processes, carbon dioxide, ethane and heavier hydrocarbons are separated or recovered as a mixture. It is then desirable to separate the carbon dioxide from the remaining hydrocarbons, sometimes called NGL (natural gas liquids). When carbon dioxide is distilled or fractionated from the hydrocarbons, an azeotrope of carbon dioxide and ethane is formed at an overhead point in the distillation column. At this point no more ethane is separated from the carbon dioxide. Generally, unless it is desirable to recover the carbon dioxide, the carbon dioxide is vented unless the concentration of ethane in the azeotrope is such that environmental regulations make it necessary to burn the ethane-carbon dioxide mixture. Flaring is frequently an expensive and difficult process, especially in areas where the amount and concentration of the gas being flared randomly varies with various operating or producing conditions. In processes where it is desirable to recover the carbon dioxide, for example, tertiary recovery processes, the unseparated ethane is lost.

The ethane in the carbon dioxide is a valuable hydrocarbon. This invention is concerned with separating and recovering ethane along with the other hydrocarbons that might be in a carbon dioxide-ethane mixture derived from a prior process.

SUMMARY OF THE INVENTION

A mixture of carbon dioxide and ethane derived from a prior separation stage or recovery process is separated by liquid-liquid extraction. One of the liquids is a liquid azeotrope of carbon dioxide and ethane. The extraction liquid is a liquid hydrocarbon with more carbon atoms than ethane, that is, a hydrocarbon having at least three carbon atoms. In the extraction unit, ethane follows the extraction hydrocarbon.

The liquid-liquid extraction stage may be preceded by a first stage distillation column operated to produce a liquefied azeotrope of carbon dioxide-ethane. The liquid-liquid extraction stage may be followed by distillation of the ethane-heavier hydrocarbon mixture produced by the extraction stage.

BRIEF DESCRIPTION OF THE DRAWING

The drawing is a schematic representation of a liquid-liquid extraction process with two optical distillation stages for separating a mixture of carbon dioxide and ethane.

DETAILED DESCRIPTION

In the processing of gases containing carbon dioxide and ethane, for example, natural gas, there are times when it is necessary to remove carbon dioxide. For example, natural gas is predominantly methane. The methane is frequently mixed with carbon dioxide, ethane and other heavier hydrocarbons. After the methane is separated, the mixture of carbon dioxide, ethane and other hydrocarbons is processed to separate the carbon dioxide. It is well known that some of the ethane follows the carbon dioxide stream because ethane and carbon dioxide form an azeotrope. The composition of the ethane-carbon dioxide azeotrope depends on the operating conditions of the fractionation column. Conventionally, the distillation of a mixture of carbon dioxide and ethane will result in a carbon dioxide purity of only sixty-five to seventy-five mole percent. This ethane concentration is unacceptably high for venting the carbon dioxide. Moreover, if the volume of carbon dioxide is sufficiently large, the ethane is worth recovering. This disclosure pertains to separating carbon dioxide from ethane and any heavier hydrocarbons that might be present.

Accordingly, a mixture of carbon dioxide and ethane, with or without other hydrocarbons, is passed through feed inlet line 11 into first stage distillation column 13 at a point which is between overhead effluent line 15 and bottoms liquid line 17. This mixture of carbon dioxide and ethane has been derived from a prior carbon dioxide separation stage or recovery process. For purposes of this disclosure, the previous stage or process is considered a carbon dioxide separation stage or recovery process if any fluid stream containing carbon dioxide and ethane is separated or developed. For example, the prior stage may have been a methane separation stage wherein a stream of carbon dioxide and ethane with or without heavier hydrocarbons is developed. The mixture may be gaseous, liquid, or a mixture of gaseous, liquid, or a mixture of gas and liquid phases. Usually the mixture will be a two phase mixture at an elevated pressure. The pressure of the mixture will be at or above the pressure of the distillation column. The operation of distillation columns is well known and will not be discussed in detail.

During operation of the column, an azeotrope of carbon dioxide and ethane will be formed in the upper section of the rectification section of the column. This azeotrope exits the column through overhead effluent line 15. The concentration of carbon dioxide and ethane in the azeotrope will depend on the column overhead operating conditions. As shown, the carbon dioxide-ethane azeotrope overhead effluent fluids are cooled in first condenser 19 to condense all the overhead effluent fluids and form a liquefied azeotrope. A liquid azeotrope is needed for the next stage of the process. Preferably, the condenser will be operated at a temperature above minus 69.9° F. to prevent the formation of solid carbon dioxide. At least a part of the condensed overhead fluids is recycled to the column through reflux inlet line 21.

The ethane and heavier hydrocarbons in the feed mixture which are liquefied in the column are removed through bottoms liquid line 17 and recovered.

The remaining liquid azeotrope in line 21 is passed into liquid-liquid extraction column 23. At the same time, a hydrocarbon extraction liquid is passed into the extraction through extraction liquid inlet line 25. The extraction liquid is a hydrocarbon with three or more carbon atoms and is added at a rate and in an amount sufficient to remove all or a substantial portion of the ethane from the azeotrope liquid. In the extraction unit, the carbon-dioxide-ethane azeotropic liquid and the extraction liquid mix in sufficient portion for the ethane to be extracted by the heavier hydrocarbon liquid. Some carbon dioxide may be dissolved in the hydrocarbon liquid, but the amount can be kept low by operating the extraction unit at lower temperatures. The ethane and extraction liquid have a different specific gravity from the liquid carbon dioxide. The two liquids in the extraction unit separate if the unit is operated under conditions such that the carbon dioxide and hydrocarbons are immiscible. The lighter of two liquids exits the extraction unit by way of overhead liquid line 27 and as shown is passed to second stage distillation column 29. The heavier liquid exits by way of bottoms liquid line 31. For illustrative purposes, the hydrocarbon extraction liquid is shown as propane and the ethane-propane mixture as being the lighter liquid and passing overhead through line 27 to distillation column 29. However, the situation could be reversed in which case the liquid in bottoms liquid line 31 would be passed to column 29 instead of the liquid in exit line 27. Moreover, the flows of the azeotropic liquid and the extraction into extraction unit 23 could be reversed.

As shown, the liquid mixture of ethane and propane is passed to second stage distillation column 29 where the ethane and extraction liquid are separated with ethane passing overhead through effluent exit line 33 into overhead condenser 35 where a portion of the effluent gases are cooled and condensed. The cooled fluids are flowed into separator 37 and the liquids are returned through reflux line 39 to the column and the ethane recovered through gas line 41.

The separated heavier hydrocarbons exit the column through bottom liqud line 43 where at least a portion of the extractive type hydrocarbons are passed through cooler 45 and through inlet line 25 in the extraction unit.

In typical fashion distillation columns 13 and 29 are equipped with side heaters or reboilers represented by reboilers 47. These reboilers and overhead condensers 19 and 35 are used to balance the heat loads of the columns.

Reasonable variations and modifications are possible within the scope of this disclosure without departing from the spirit and scope of this invention.

The embodiments of the invention in which an exclusive property or privilege is claimed are defined as follows:

1. A method for separating a mixture of carbon dioxide and ethane derived from a prior separation stage, said method comprising:
    (a) passing a liquid azeotrope of carbon dioxide and ethane into an extraction unit, said azeotrope having been derived from a prior carbon dioxide separation stage;
    (b) passing a liquid hydrocarbon comprised of at least three carbon atoms into said extraction unit in a manner and quantity such that said liquid azeotrope and said liquid hydrocarbon mix and a substantial portion of said ethane in said azeotrope is extracted with said liquid hydrocarbon;
    (c) removing a first fluid stream from said extraction unit, said first fluid having a greater concentration of carbon dioxide than said liquid azeotrope, and
    (d) removing a second fluid stream from said extraction unit, said second fluid being comprised of said hydrocarbon liquid and ethane extracted from said liquid azeotrope.

2. In the method of claim 1 wherein the method includes the following additional steps:
    (e) passing a fluid mixture comprised of carbon dioxide and ethane into a first distillation column to separate ethane from said mixture and to form an overhead azeotrope of carbon dioxide and ethane, said fluid mixture having been derived from a prior carbon dioxide separation stage, and
    (f) liquefying at least a portion of said azeotrope to form at least a portion of the liquid azeotrope used in step (a).

3. In the method of claim 2 wherein the method includes the following additional step:
    (g) passing at least a portion of said second fluid produced in step (d) to a second distillation column to separate at least a portion of the hydrocarbons having at least three carbon atoms to form at least a portion of the hydrocarbon used in step (b).

4. In the method of claim 1 wherein the method includes the following additional step:
    (e) passing at least a portion of said second fluid produced in step (d) to a distillation column to separate at least a portion of the hydrocarbons having at least three carbon atoms to form at least a portion of the hydrocarbon used in step (b).

* * * * *

UNITED STATES PATENT OFFICE
CERTIFICATE OF CORRECTION

PATENT NO. : 4,311,495

DATED : January 19, 1982

INVENTOR(S) : Ralph E. Styring, Jr.

It is certified that error appears in the above-identified patent and that said Letters Patent are hereby corrected as shown below:

In column 4, line 8, after the words "comprised of" and before the words "at least" insert ---at least one hydrocarbon having---.

Signed and Sealed this

Eighteenth Day of May 1982

[SEAL]

Attest:

GERALD J. MOSSINGHOFF

Attesting Officer — Commissioner of Patents and Trademarks